(12) United States Patent
Zrimsek et al.

(10) Patent No.: US 11,598,717 B2
(45) Date of Patent: Mar. 7, 2023

(54) SYSTEMS AND METHODS FOR DISCRIMINATION OF TISSUE TARGETS

(71) Applicant: CHEMIMAGE CORPORATION, Pittsburgh, PA (US)

(72) Inventors: Alyssa Zrimsek, Pittsburgh, PA (US); Matthew Nelson, Harrison City, PA (US); Lei Shi, Pittsburgh, PA (US); Heather Gomer, Sewickley, PA (US); Shawna Tazik, Pittsburgh, PA (US)

(73) Assignee: CHEMIMAGE CORPORATION, Pittsburgh, PA (US)

( * ) Notice: Subject to any disclaimer, the term of this patent is extended or adjusted under 35 U.S.C. 154(b) by 0 days.

(21) Appl. No.: 17/121,247

(22) Filed: Dec. 14, 2020

(65) Prior Publication Data

US 2021/0181101 A1 Jun. 17, 2021

Related U.S. Application Data

(60) Provisional application No. 62/947,261, filed on Dec. 12, 2019.

(51) Int. Cl.
*G01N 21/3563* (2014.01)
*H04N 5/225* (2006.01)
(Continued)

(52) U.S. Cl.
CPC ......... *G01N 21/3563* (2013.01); *A61B 90/30* (2016.02); *A61B 90/361* (2016.02);
(Continued)

(58) Field of Classification Search
CPC ... G01J 4/00; G01J 3/45; G01N 21/21; G02B 21/0028; G02B 21/16
See application file for complete search history.

(56) References Cited

U.S. PATENT DOCUMENTS 6,419,361 B2 * 7/2002 Cabib ...................... G01J 3/26
351/221
6,556,853 B1 * 4/2003 Cabib ................... G01J 3/2823
600/407

(Continued)

OTHER PUBLICATIONS

Birefringence measurement of biological tissue based on polarization; Wang—2018. (Year: 2018).*

(Continued)

*Primary Examiner* — Luis Perez-Fuentes
(74) *Attorney, Agent, or Firm* — DLA Piper LLP (US)

(57) ABSTRACT

Systems for and methods for detecting samples and other compounds of interest are disclosed herein. The system can include an illumination source that is configured to emit light in a variety of different wavelength bands, an optical filter, a camera chip, and an optical path configured to direct the light emitted by the first illumination source at a target and direct the light reflected from the target to the at least one camera chip. The illumination source and the optical filter are transitionable between a first tuning state corresponding to a target tissue and a second tuning state corresponding to a background tissue. The system can be configured to record images at the different tuning states and generate a score image corresponding to the target tissue based on the recorded images.

15 Claims, 11 Drawing Sheets

(51) Int. Cl.
*A61B 90/00* (2016.01)
*A61B 90/30* (2016.01)
*G01N 21/17* (2006.01)

(52) U.S. Cl.
CPC ......... *H04N 5/2254* (2013.01); *H04N 5/2256* (2013.01); *H04N 5/2258* (2013.01); *A61B 2090/309* (2016.02); *G01N 2021/1765* (2013.01); *G01N 2201/061* (2013.01)

(56) References Cited

U.S. PATENT DOCUMENTS

| 10,151,634 | B2* | 12/2018 | Abdulhalim ............ G01J 3/447 |
| 10,634,560 | B2* | 4/2020 | Abdulhalim ......... G02B 27/286 |
| 11,202,589 | B2* | 12/2021 | Albuquerque ..... A61B 5/14555 |
| 2006/0004292 | A1 | 1/2006 | Beylin |
| 2013/0281845 | A1 | 10/2013 | Luiken |
| 2013/0296709 | A1 | 11/2013 | Zuzak et al. |
| 2014/0288419 | A1 | 9/2014 | Wang et al. |
| 2018/0267290 | A1 | 9/2018 | Boamfa et al. |
| 2019/0195689 | A1 | 6/2019 | McQuilkin et al. |

OTHER PUBLICATIONS

Modeling optical behavior of birefringent tissues for evaluation polarized light; 2009. (Year: 2009).*
What is an Interferometer—LIGO Lab Caltech; 2021. (Year: 2021).*
Library—USPTO; 2022. (Year: 2022).*

* cited by examiner

SYSTEMS AND METHODS FOR DISCRIMINATION OF TISSUE TARGETS

CROSS-REFERENCE TO RELATED APPLICATION

The present application claims priority to U.S. Provisional Patent Application No. 62/947,261, titled DISCRIMINATION OF TISSUE TARGETS WITH A COMBINATION OF SOURCE MODULATION AND IMAGING FILTERING IN THE VIS-NIR-SWIR, filed Dec. 12, 2019, which is hereby incorporated by reference herein in its entirety.

BACKGROUND

Visualization of tissues and anatomical structures during surgery is critical to avoid unintended cutting or harming of tissue. Visualization of surgical sites is challenging for even the most experienced surgeons because of the presence of blood, fat, arteries, veins, muscle, and fascia, all of which obstruct the field of view. Real-time intraoperative imaging tools that are non-contact and reagentless are needed in order to assist surgeons in accurately visualizing surgical sites and locating obscured targets. Molecular chemical imaging has been used to visualize tissues and anatomical structures with technologies including conformal filters (CF), liquid crystal tunable filters (LCTF), and multi-conjugate filters (MCF). However, there is a continuing desire to further improve the visualization of tissues and anatomical structures in novel ways in order to provide better margins, depth of penetration, and identification of structures.

SUMMARY

The below summary is to briefly indicate the nature and substance of the invention. However, the summary is submitted with the understanding that it is not to be used to interpret or limit the scope or meaning of any claims.

In one embodiment, the present disclosure is directed to an apparatus or system that can comprise: an illumination source that is configured to emit light, the light comprising at least one of ultraviolet (UV), visible (VIS), near infrared (NIR), visible-near infrared (VIS-NIR), shortwave infrared (SWIR), extended shortwave infrared (eSWIR), near infrared-extended shortwave infrared (NIR-eSWIR), mid-wave infrared (MIR), or long-wave infrared (LWIR) light; an optical filter; at least one camera chip; and an optical path configured to direct the light emitted by the first illumination source at a target and direct the light reflected from the target to the at least one camera chip. The illumination source and the optical filter can be transitionable between a first tuning state corresponding to a target tissue and a second tuning state corresponding to a background tissue. The at least one camera chip can be configured to: record a first image when the illumination source and the optical filter are in the first tuning state, record a second image when the illumination source and the optical filter are in the second tuning state, and generate a score image corresponding to the target tissue based on the first image and the second image.

The illumination source can include a modulated illumination source or a non-modulated or broadband illumination source (e.g., a quartz tungsten halogen illumination source).

In another embodiment, the illumination source comprises at least one of a light emitting diode (LED), supercontinuum laser, organic light emitting diode (OLED), electroluminescent device, fluorescent light, gas discharge lamp, metal halide lamp, xenon arc lamp, or induction lamp.

In another embodiment, wherein the illumination source can comprise a first illumination source, the apparatus can further comprise a second illumination source that emits at least one of UV, VIS, NIR, VIS-NIR, SWIR, eSWIR, NIR-eSWIR, MIR, or LWIR light. The second illumination source can include a modulated illumination source or a non-modulated or broadband illumination source (e.g., a quartz tungsten halogen illumination source).

In another embodiment, the optical filter can be selected from the group consisting of a liquid crystal filter, a liquid crystal on silicon (LCoS) that can be controlled to alter the luminous flux in near real time or in real time, a rotating filter wheel, a MCF, and a CF.

In one embodiment, the apparatus can further comprise an optic coupled to the optical path, the optic configured to direct a first portion of the light emitted by the first illumination source at the first camera chip for generating the first image from the first portion of the light and direct a second portion of the light emitted by the first illumination source at the second camera chip for generating the second image from the second portion of the light.

In one embodiment, the at least one camera chip comprises a focal plane array sensitive to at least one of UV, VIS, NIR, VIS-NIR, SWIR, eSWIR, NIR-eSWIR MIR, or LWIR light.

In one embodiment, there is a method of analyzing a biological sample, the method comprising emitting light from an illumination source that emits at least one of UV, VIS, NIR, VIS-NIR, SWIR, eSWIR, NIR-eSWIR, MIR, or LWIR light; transmitting the light via an optical path at the biological sample; collecting the light reflected from the biological sample on at least one camera chip; recording a first image when the illumination source and the optical filter are in the first tuning state; recording a second image when the illumination source and the optical filter are in the second tuning state; and generating a score image corresponding to the target tissue based on the first image and the second image.

In another embodiment, the present disclosure is directed to methods using or operating any of the aforementioned embodiments of apparatuses or systems.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings.

DETAILED DESCRIPTION

Figure 1:
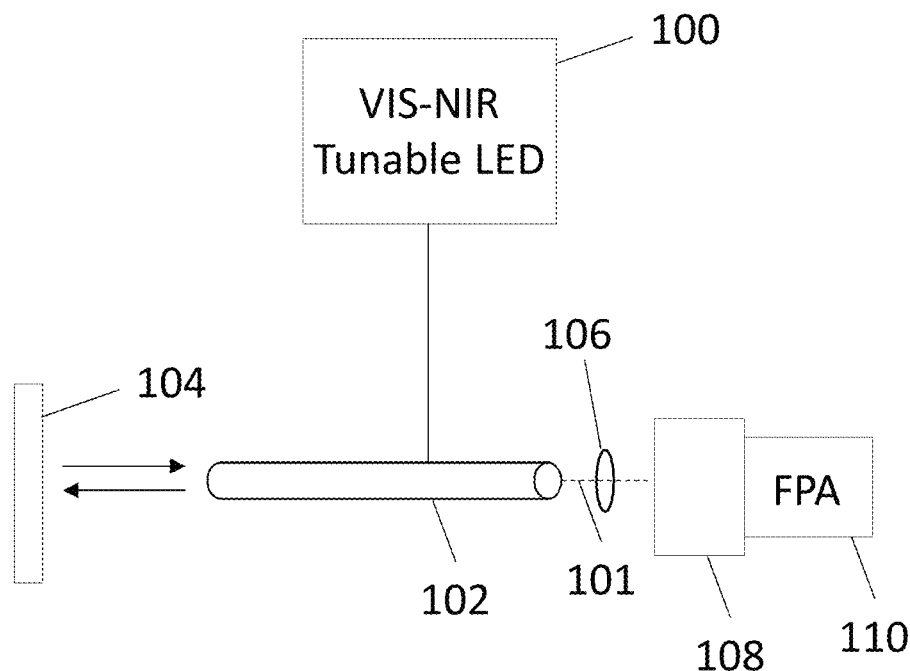
FIG. 1 illustrates one embodiment of an apparatus and method of analysis whereby a tunable illumination source generates VIS light and NIR light and the LCTF stage is positioned in an optical path between an endoscope and a VIS-NIR camera chip.

This disclosure is not limited to the particular systems, methods, and computer program products described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The embodiments described below are not intended to be exhaustive or to limit the teachings to the precise forms disclosed in the following detailed description. Rather, the embodiments are chosen and described so that others skilled in the art may appreciate and understand the principles and practices of the present teachings.

The disclosure contemplates systems, methods, and computer program products that are designed to illuminate a sample with illuminating photons, collect interacted photons from the sample by way of a camera chip, generate two or more sample images from the interacted photons that have been collected and imaged by the camera chip, and fuse the two or more sample images so as to generate a target score image. The target score image is generated by applying mathematical operations to the two or more sample images in order to fuse the two or more sample images. The target score image has greater contrast and information than would be possible with any one of the two or more sample images that are formed from the interacted photons. Further details of the disclosure are provided below.

Illumination Source

The illumination source is not limited and can be any source that is useful in generating the photons necessary for illumination while meeting other ancillary requirements, such as power consumption, emitted spectra, packaging, thermal output, and so forth. In some embodiments, the illumination source is a LED, incandescent lamp, halogen lamp, supercontinuum laser, OLED, electroluminescent device, fluorescent light, gas discharge lamp, metal halide lamp, xenon arc lamp, induction lamp, or any combination of these illumination sources. In some embodiments, the illumination source is a tunable illumination source, which means that the photons that are generated by the illumination source can be selected to be within any desired wavelength range. In some embodiments, the illumination source generates monochromatic photons, which are photons that have a single wavelength. In some embodiments, the illumination source generates polychromatic photons, which are photons that have multiple wavelengths or a passband, which is a range of photon wavelengths. The selected wavelength of the tunable illumination source is not limited and can be any passband within the UV, VIS, NIR, VIS-NIR, SWIR, eSWIR, NIR-eSWIR, MIR, and LWIR ranges.

In some embodiments, the illumination source is a supercontinuum laser, and the supercontinuum laser generates a continuous output of photons over an entire wavelength range. Supercontinuum lasers appear to generate white because multiple nonlinear optical processes act together on a pumped laser beam, thereby causing spectral broadening of the original pumped laser beam. For example, the pumped laser beam can be passed through a microstructured optical fiber. The supercontinuum laser can in some embodiments achieve a continuous output over a wavelength range of about 400 nm to about 2400 nm. In other embodiments, the supercontinuum laser generates a continuous output in the range of UV, VIS, NIR, VIS-NIR, SWIR, eSWIR, NIR-eSWIR, MIR, LWIR, or combinations of one or more of the preceding ranges.

The above ranges of light correspond to wavelengths of about 180 nm to about 380 nm (UV), about 380 nm to about 720 nm (VIS), about 400 nm to about 1100 nm (VIS-NIR), about 850 nm to about 1800 nm (SWIR), about 1200 nm to about 2450 nm (eSWIR), about 720 nm to about 2500 nm (NIR-eSWIR), about 3000 nm to about 5000 nm (MIR), or about 8000 nm to about 14000 nm (LWIR). The above ranges may be used alone or in combination of any of the listed ranges. Such combinations include adjacent (contiguous) ranges, overlapping ranges, and ranges that do not overlap. The combination of ranges may be achieved by the inclusion of multiple illumination sources, by filtering illumination sources, or by the addition of at least one component, such as phosphors and/or quantum dots, that convert high energy emissions, such as UV or blue light, into lower energy light having longer wavelengths.

In some embodiments, the illumination source is modulated. As used herein, when an illumination source is "modulated," it means that the wavelength passbands of light that are generated by the illumination source are selectable within at least one desired spectral range. The light can be a single wavelength or contain multiple wavelengths with variable spectral shape. Such modulation of the illumination sources is not limited and is alternatively referred to as "illumination source modulation." In some embodiments, the illumination source is modulated only by controlling the brightness, or luminous flux, of the illumination source. For example, an illumination source may be operated at lower power in order to reduce the luminous flux of the illumination source, effectively dimming the illumination source at selected wavelengths of light or the full spectral range. Alternatively, the illumination source is modulated by positioning a neutral density filter between the illumination source and the sample to be analyzed, which reduces the luminous flux that reaches the sample.

In some embodiments, the illumination source is an array of illuminating elements, and each illuminating element emits a selected wavelength of light. In such embodiments, the luminous flux and/or emitted spectrum of the illuminating elements, either alone or in groupings of the illuminating elements, is adjusted and/or controlled. This alters the overall emitted wavelengths of light and the luminous flux of the wavelengths emitted by the illumination source.

When an illuminating element is included as part of an illumination array and an illumination source, the illuminating element must be capable of at least one of rapid response to control inputs, narrow light bandwidth, and the ability to quickly and predictably change the luminous flux that is emitted from the illuminating element. Examples of such useful illuminating elements that are suitable for inclusion within the illuminating array include light emitting diodes (LED), supercontinuum laser, organic light emitting diodes (OLED), electroluminescent devices, fluorescent lights, gas discharge lamps, metal halide lamps, xenon arc lamps, induction lamps, or any combination of these illumination sources. The selected wavelength of each illuminating element is not limited and can be any passband or wavelength emitted by the photoelectric effect or photon excitation within the UV, VIS, NIR, VIS-NIR, SWIR, eSWIR, NIR-eSWIR, MIR, and LWIR ranges.

In some embodiments, illumination source modulation is achieved by positioning a filter in the optical path between the illumination source and the sample. The choice of filter is not limited. In some embodiments, the filter is a fixed filter such as a bandpass filter that transmits light selected wavelengths. Fixed filters include absorptive filters, interference filters, and dichroic filters. In some embodiments, the filter is a neutral density filter. The neutral density filter can have a fixed reduction in luminous flux, or it can be variable and thereby controlled. In some embodiments, the filter is a liquid crystal filter or a LCoS that can be controlled to alter the luminous flux in near real time or in real time. In some embodiments, the filter is a mechanical, electromechanical, or micro electro mechanical device that modulates the luminous flux. Examples of mechanical filters include rotating filter wheels with at least one fixed filter. Examples of electromechanical filters include fixed filters that are moved by one or more of electric motors, solenoids, and servo-mechanisms. Examples of micro electro mechanical devices include digital micromirror devices. Digital micromirror devices are available under the trade name DLP® from Texas Instruments Incorporated of Dallas, Tex.

Image Modulation

In some embodiments, an image that is generated from collected photons is modulated. Examples of such modulation are not limited and can be achieved by various devices. The modulation of the collected photons, and thereby the image, can be achieved by inserting one or more of CFs, MCFs, or LCTFs. In some embodiments, the CF, MCF, or LCTF is combined with the source modulation described above. In some embodiments, the inclusion of source modulation permits the omission of a CF, MCF, or LCTF that would otherwise be required. The combination of a tunable source with a single stage LCFT, when compared with an illumination source combined with an MCF or CF, will have faster tuning speeds and higher throughput because MCFs/CFs contain multiple LCTF stages. The combination of a single stage with the tunable source will also all you to create unique illumination shapes as you would with an MCF or CF. Faster tuning speeds are important because they permit real time or near real time image rendering, which assists medical personnel in viewing samples or surgical sites. In still further embodiments, the combination of one or more tunable illumination sources with one or more of a CF, MCF, or LCTF permits greater precision in selecting wavelengths simultaneously for illumination and detection.

The combination of the tunable illumination source and the filters in the optical path of the collected photons is not limited. In one embodiment, the illumination source is a VIS-NIR-SWIR tunable LED device. In another embodiment, the illumination source is a tunable VIS-NIR LED, and the photons are collected by a CF, MCF, or LCTF. In another embodiment, the illumination source is a tunable VIS-SWIR LED, and the photons are collected by CFs, MCFs, or LCTFs. In another embodiment, the illumination source is a tunable SWIR LED, and the photons are collected by CFs, MCFs, or LCTFs. In another embodiment, the illumination source is a tunable VIS-NIR-SWIR LED, and the photons are collected by CFs, MCFs, or LCTFs. In another embodiment, the illumination source is a combination of a tunable VIS-NIR LED and halogen lamp with SWIR, and the photons are collected by CF, MCF, or LCTF.

In some embodiments, there is at least one camera chip that collects and images the interacted photons. In some embodiments, the at least one camera chip is characterized by the wavelengths of light that it is capable of imaging. The wavelengths of light that can be imaged by the camera chip are not limited, and include UV, VIS, NIR, VIS-NIR, SWIR, eSWIR, NIR-eSWIR. These classifications correspond to wavelengths of about 180 nm to about 380 nm (UV), about 380 nm to about 720 nm (VIS), about 400 nm to about 1100 nm (VIS-NIR), about 850 nm to about 1800 nm (SWIR), about 1200 nm to about 2450 nm (eSWIR), and about 720 nm to about 2500 nm (NIR-eSWIR). The above ranges may be used alone or in combination of any of the listed ranges. Such combinations include adjacent (contiguous) ranges, overlapping ranges, and ranges that do not overlap. The combination of ranges may be achieved by the inclusion of multiple camera chips, each sensitive to a particular range, or a single camera chip that by the inclusion of a color filter array can sense multiple different ranges.

In some embodiments, the at least one camera chip is characterized by the materials from which it is made. The materials of the camera chip are not limited and can be selected based on the wavelength ranges that the camera chip is expected to detect. In such embodiments, the camera chip comprises silicon (Si), germanium (Ge), indium gallium arsenide (InGaAs), platinum silicide (PtSi), mercury cadmium telluride (HgCdTe), indium antimonide (InSb), colloidal quantum dots (CQD), or combinations of any of these. In some embodiments, the at least one camera chip is a focal plane array (FPA), which is an array of light-sensing pixels positioned at the focal plane of a lens. In some embodiments, the camera chip is characterized by its electrical structure. The electrical structure is not limited. In some embodiments, the camera chip includes a charge coupled device (CCD) or a complementary metal oxide semiconductor (CMOS) image sensor. It should be noted that the materials listed above can each be used with either electrical structure to form the final camera chip, and that each of the above can be formed as a FPA.

Tissues and Target Discrimination

The apparatus and methods of the disclosure can detect any useful biological or physiological structures by generating score images. A score image is the result of mathematical manipulation of two or more images to generate a contrast of the target. The score images are not limited and include data collected with at least one passband of light.

In the present disclosure, by broadening the light that is gathered from the at least one passband of light in at least the VIS-NIR and SWIR regions (among others), there is a significant increase in the spectral information available for target discrimination, thereby improving the ability to resolve targets of interest in the presence of obscuration. For example, the absorption spectra of hemoglobin, myoglobin, and beta-carotene are in the VIS range, whereas the absorption spectra of water, lipids, adipose tissue, and fats are primarily the NIR and SWIR range. In addition, the combination of VIS-NIR and SWIR light can aid in the detection through obscuration as SWIR light can penetrate deeper into tissues. It should be noted, however, that the above biological structures are not exhaustive, and that any organ, tissue, or biological sample can be analyzed by the apparatus and/or methods of the disclosure.

In some embodiments, source modulation is performed so as to generate an amount of contrast that is required to achieve target discrimination. In some embodiments, the source modulation is performed by varying the luminous flux and/or wavelengths that are outputted by the tunable illumination source. Tunable illumination sources are described above. In some embodiments, source modulation is achieved by varying the luminous flux of the LEDs themselves through increasing or decreasing the supplied current. In some embodiments, source modulation is achieved by varying the configuration of filters that are positioned in the optical path between the tunable illumination source and the sample or between the tunable illumination source and another component of the system or apparatus.

In some embodiments, real-time detection is achieved by tuning the illumination source or by configuring an optical filter to modulate the luminous flux that emanates from the illumination source. In one embodiment, one or more CFs are positioned in association with the tunable illumination source. In another embodiment, one or more MCFs are positioned in association with the tunable illumination source. In yet another embodiment, one or more LCTFs are positioned in association with the tunable illumination source.

Imaging Systems for Target Discrimination

In one embodiment, a single camera variant is provided. Referring now to FIG. 1, a tunable LED illumination source 100 is capable of generating photons in the VIS-NIR spectral range. During operation, VIS-NIR light is transmitted through an endoscope 102 to a target 104, which can be a tissue sample or a surgical site. After the photons interact with the target, the interacted photons are transmitted through the endoscope 102 and through at least one lens 106 to a LCTF stage 108. After being modulated by the LCTF stage 108, the interacted photons which have now been modulated by both the tunable LED illumination source 100 and the LCTF stage 108 are collected by a camera chip 110 that is a VIS-NIR sensitive focal plane array (FPA). The FPA is a CCD camera chip, but this is not limited and can be substituted for a CMOS camera chip if desired. A LCTF 108 is placed in the optical path 101 between the lens 106 and the VIS-NIR FPA camera chip 110 in order to modulate the interacted photons before they are collected by the FPA camera chip 110.

Figure 7:
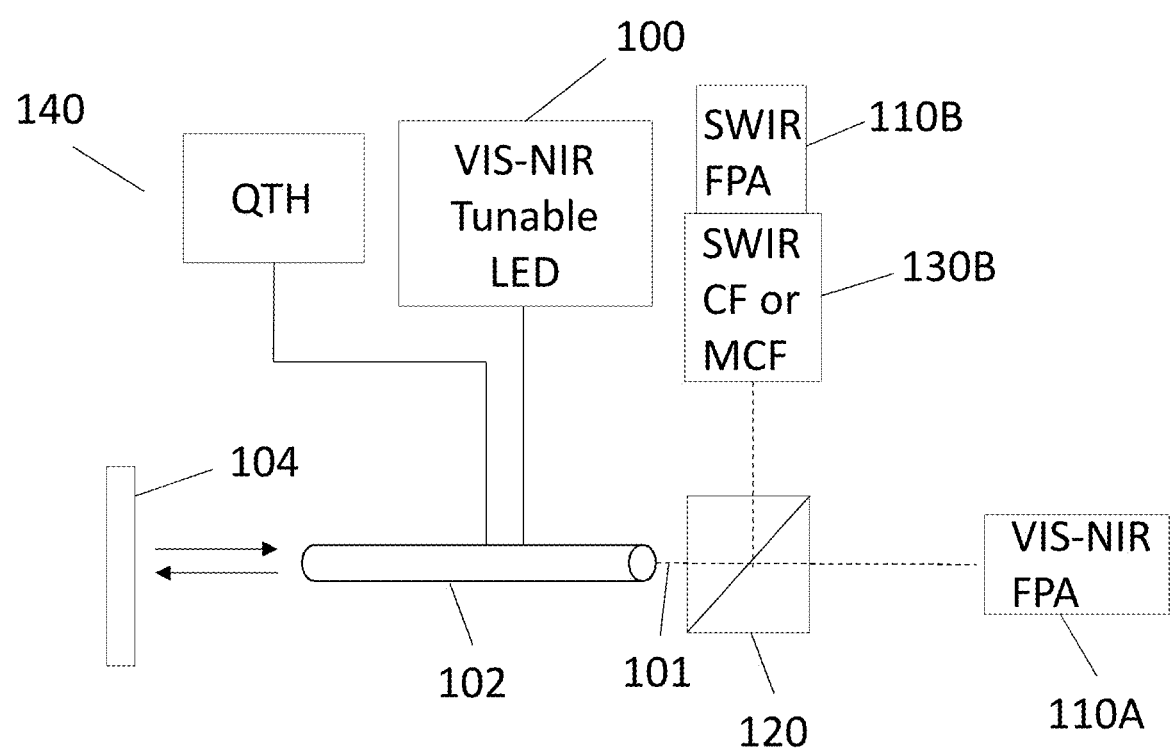
FIG. 7 illustrates one embodiment of an apparatus and method of analysis whereby a tunable illumination source operates in conjunction with a halogen lamp illumination source in order to transmit mixed spectrum light to an optic that reflects SWIR light through a CF or MCF to a SWIR FPA camera chip and transmits VIS-NIR light to a VIS-NIR FPA camera chip.
Figure 8:
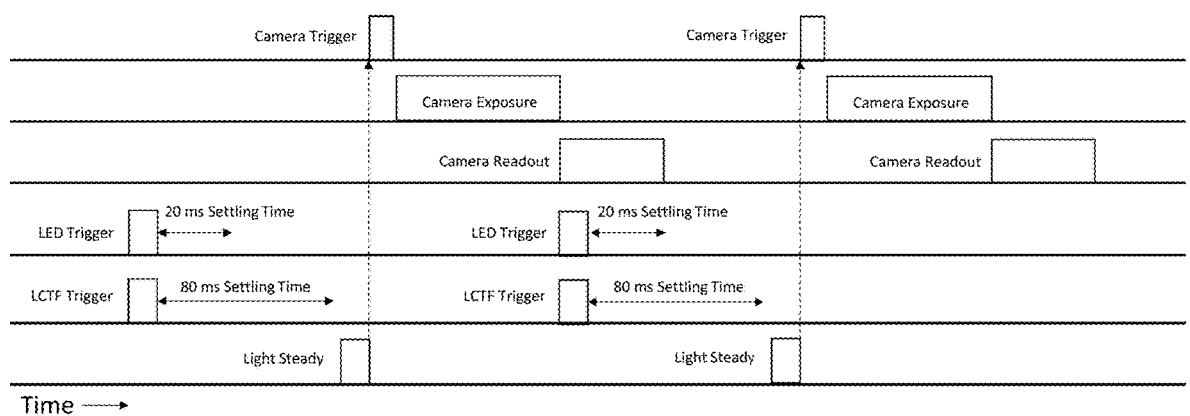
FIG. 8 illustrates a timing diagram for a single-camera image acquisition system.

In one embodiment, the LED illumination source 100, the camera chip 110, LCTF stage 108, and/or the other components of the system can be synched for data collection. For example, FIG. 8 is an illustrative timing diagram for a single-camera image acquisition system, such as the example shown in FIG. 1. As can be seen in the diagram, the triggers for the tunable LED illumination source 100 and the LCTF stage 108 can be synched with the trigger for the camera chip 110 to ensure proper image acquisition. As can be seen, the time to collect the T1 and T2 images=2×(camera exposure time)+(light steady time). In various embodiments, adding a second camera (i.e., dual-polarization), as shown in the examples in FIGS. 2, 3, 6, and 7, can increase the frame rate of the score image generated by the system. In various embodiments, adding more LED illumination sources to the image acquisition system can decrease the image acquisition time. In various embodiments, adding an external illumination ring separate from the LED assembly can decrease the image acquisition time.

Figure 2:
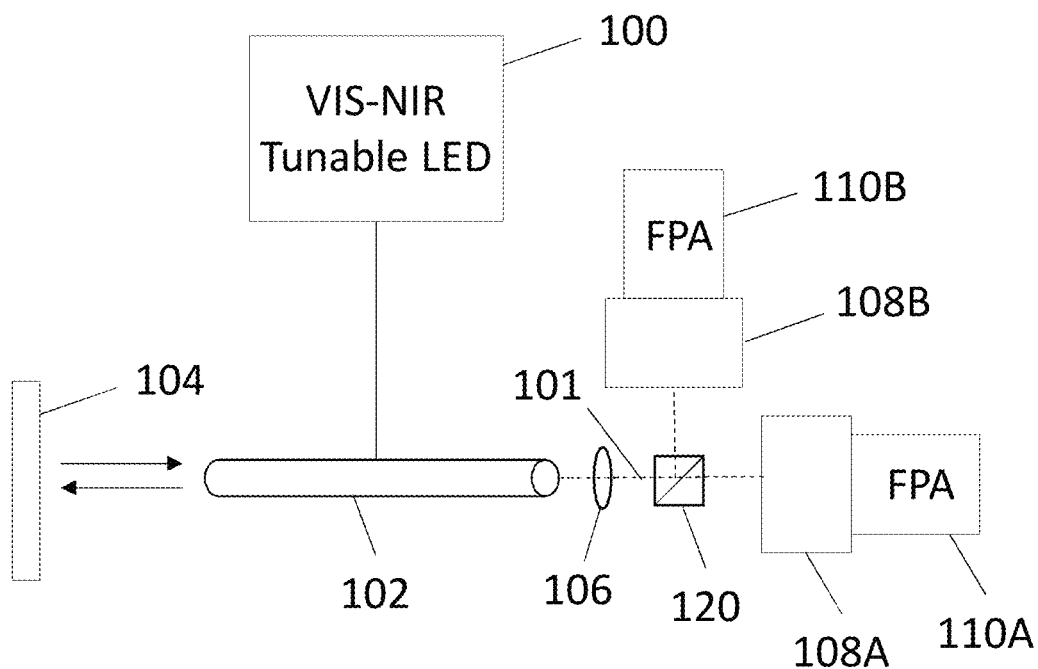
FIG. 2 illustrates one embodiment of an apparatus and method of analysis whereby a tunable illumination source generates VIS light and NIR light and a LCTF stage is positioned in an optical path between an endoscope and VIS-NIR camera chips.

In another embodiment, a dual camera variant is provided. Referring now to FIG. 2, a tunable LED illumination source 100 generates photons in the VIS-NIR spectral range. During operation, VIS-NIR light is transmitted through an endoscope 102 to a target 104, which can be a tissue sample or a surgical site. After the photons interact with the target 104, the interacted photons are transmitted through the endoscope 102 along the optical path 101 and through at least one lens 106 to an optic 120 (e.g., a prism, mirror, and/or beamsplitter) that directs at least a first portion of the interacted photons from a second portion of the interacted photons. The first portion of the interacted photons is directed to a first LCTF stage 108A and subsequently to a first camera chip 110A that is a VIS-NIR FPA. The second portion of the interacted photons is directed to a second LCTF stage 108B and subsequently to a second camera chip 110B that is a VIS-NIR FPA. The first camera chip 110A generates a first image from the VIS-NIR light, and the second camera chip 110B generates a second image from the VIS-NIR light. The configuration illustrated in this embodiment can be beneficial because the use of dual cameras allows shorter collection times.

Figure 3:
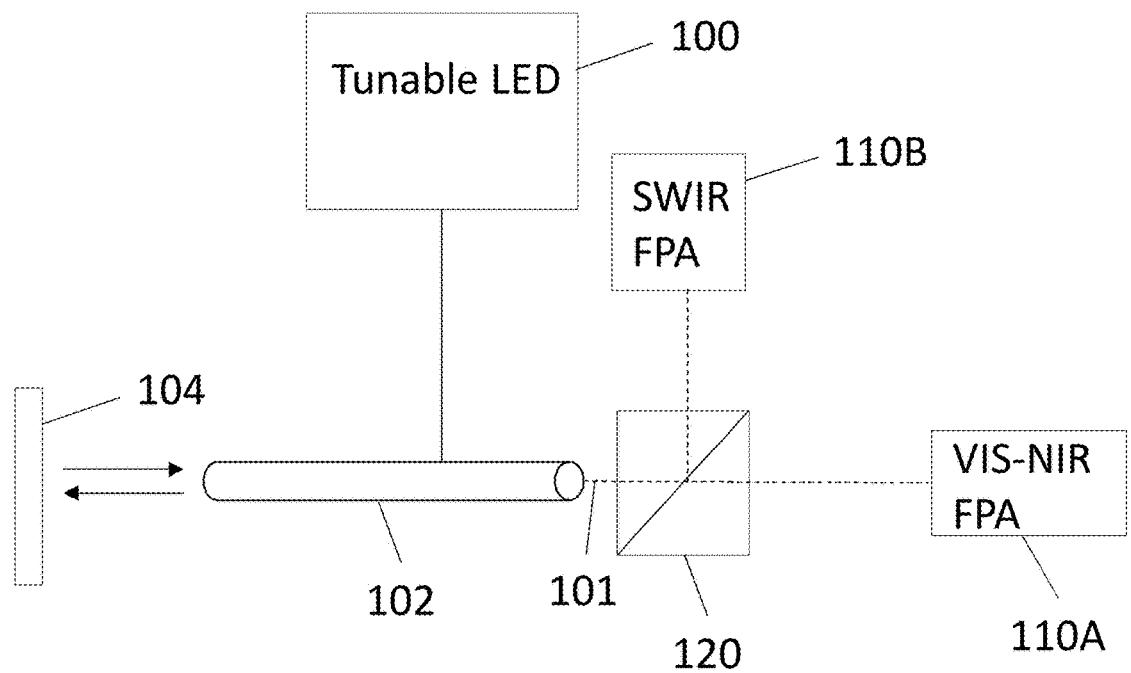
FIG. 3 illustrates one embodiment of an apparatus and method of analysis whereby a tunable illumination source operates in conjunction with an optic that transmits VIS-NIR light and reflects SWIR light, thereby transmitting VIS-NIR light to a VIS-NIR FPA camera chip and reflecting SWIR light to a SWIR FPA camera chip.

In another embodiment, a dual camera variant includes FPAs that are sensitive to and generates images from different spectra of interacted photons. Referring now to FIG. 3, a tunable LED illumination source 100 generates photons in the VIS, NIR, and SWIR spectral ranges. During operation, the VIS, NIR, and SWIR light is transmitted via an endoscope 102 to a target 104. After the photons interact with the target 104, the interacted photons are transmitted through the endoscope 102 along the optical path 101 to a optic 120. The optic 120 includes an optical filter coating that permits VIS-NIR light to pass through it, but reflects SWIR light. The VIS-NIR light that is passed through the optic 120 is directed to a first camera chip 110A that is a FPA that is sensitive to VIS-NIR light in order to generate a first image. The SWIR light that is reflected by the optic 120 is directed to a second camera chip 110B that is a FPA that is sensitive to SWIR light in order to generate a second image from the SWIR light. The configuration illustrated in this embodiment can be beneficial because the combination of VIS-NIR and SWIR light can aid in discrimination of targets through obscuration.

Figure 4:
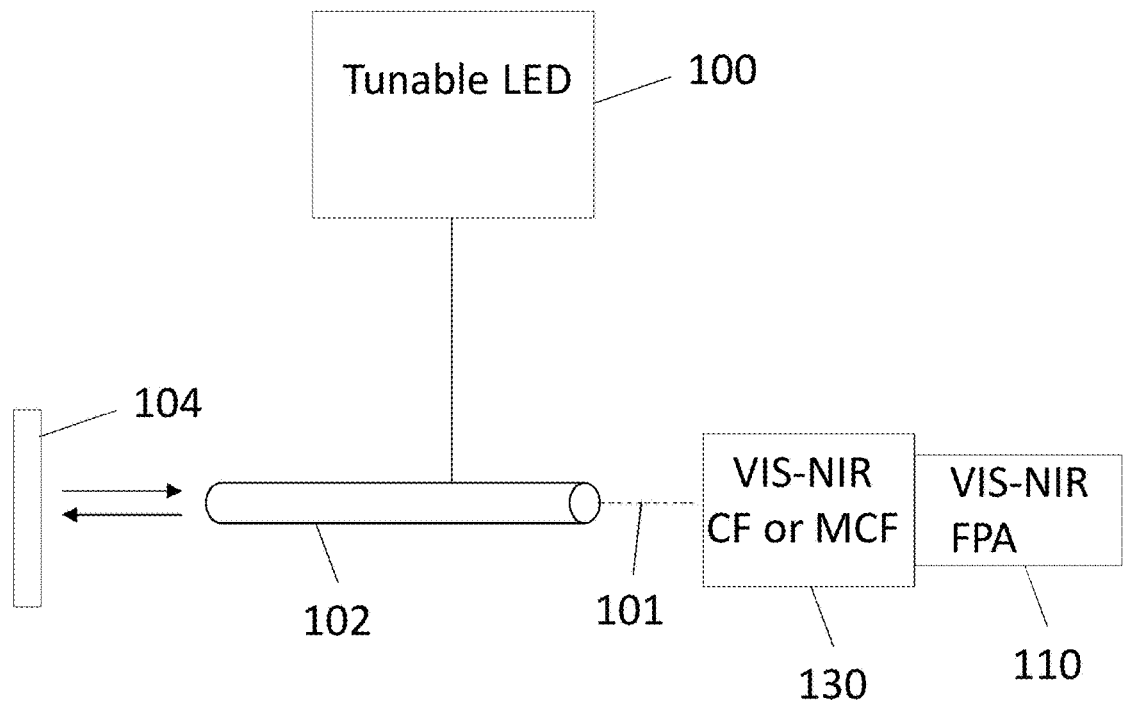
FIG. 4 illustrates one embodiment of an apparatus and method of analysis whereby a tunable illumination source operates in conjunction with a VIS-NIR FPA camera chip, and whereby a VIS-NIR CF or MCF is positioned in an optical path between an endoscope and the VIS-NIR FPA camera chip.

In another embodiment, a single camera variant includes a FPA that is sensitive to VIS-NIR light and generates images from interacted photons. Referring now to FIG. 4, a tunable LED illumination source 100 generates photons in the VIS and NIR spectral ranges. During operation, the VIS and NIR light are transmitted via an endoscope 102 to a target 104. After the photons interact with the target 104, the interacted photons are transmitted through the endoscope 102 along the optical path 101 into a CF or MCF 130, which modulates and modifies the photons. The photons, after passing through the CF or MCF 130, are transmitted to the camera chip 110 that is a VIS-NIR FPA. The VIS-NIR FPA thereby generates an image.

Figure 5:
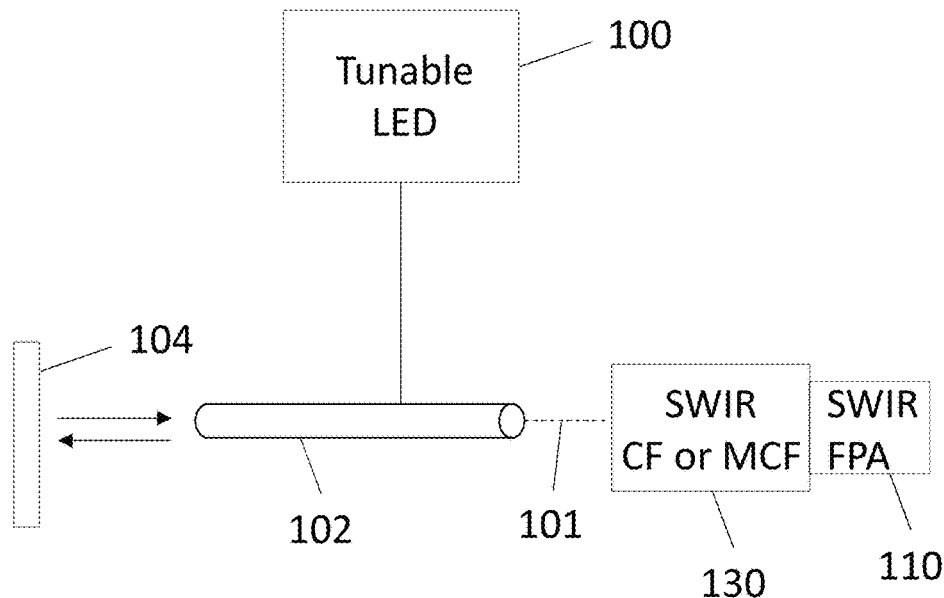
FIG. 5 illustrates one embodiment of an apparatus and method of analysis whereby a tunable illumination source operates in conjunction with a SWIR FPA camera chip, and whereby a SWIR CF or MCF is positioned in an optical path between an endoscope and the SWIR FPA camera chip.

In another embodiment, a single camera variant includes a FPA that is sensitive to SWIR light and generates images from interacted photons. Referring now to FIG. 5, a tunable LED illumination source 100 generates photons in the SWIR spectral range. During operation, the SWIR light is transmitted via an endoscope 102 to a target 104. After the photons interact with the target 104, the interacted photons are transmitted through the endoscope 102 along the optical path 101 and into a CF or MCF 130, which modulates and modifies the photons. The photons, after passing through the CF or MCF 130, are transmitted to the camera chip 110 that is a SWIR FPA. The SWIR FPA thereby generates an image.

Figure 6:
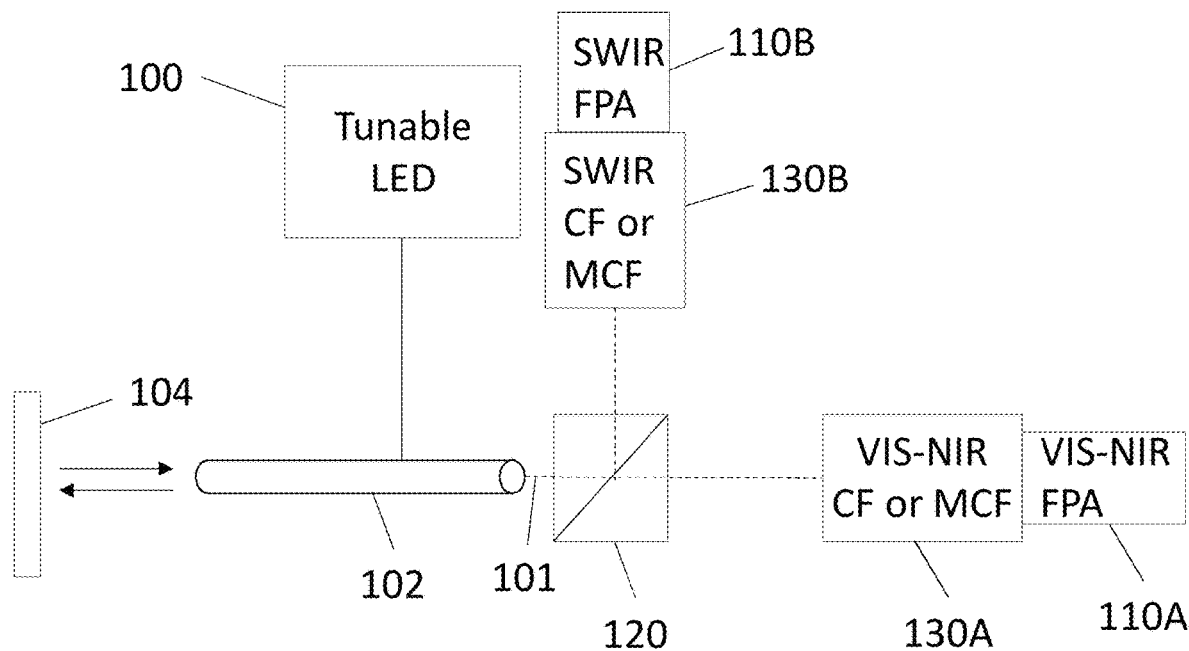
FIG. 6 illustrates one embodiment of an apparatus and method of analysis whereby a tunable illumination source operates in conjunction with an optic that transmits VIS-NIR light and reflects SWIR light, thereby transmitting VIS-NIR light through a CF or MCF to a VIS-NIR FPA camera chip and reflecting SWIR light through a CF or MCF to a SWIR FPA camera chip.

In another embodiment, a dual camera variant includes FPAs that are sensitive to different spectra of interacted photons. Referring now to FIG. 6, a tunable LED illumination source 100 generates photons in the VIS, NIR, and SWIR spectral ranges. During operation, the VIS, NIR, and SWIR light are transmitted via an endoscope 102 to a target 104. After the photons interact with the target 104, the interacted photons are transmitted through the endoscope 102 along the optical path 101 and into an optic 120. The optic 120 transmits VIS-NIR light, but reflects SWIR light. The VIS-NIR light that is transmitted by the optic 120 travels to a first CF or MCF 130A and finally to a first camera chip 110A that is a VIS-NIR FPA. The SWIR light that is reflected is transmitted to a second CF or MCF 130B, and onward to a second camera chip 110B that is a SWIR FPA. In each instance, the CF or MCF 130A, 130B is positioned in the optical path 101, between the optic 120 and the respective camera chip 110A, 110B.

In another embodiment, a dual camera, dual illumination source includes FPAs that are sensitive to different spectra of interacted photons. The illumination sources are different and emit different spectra of light. Referring now to FIG. 7, a tunable LED illumination source 100 generates photons in the VIS and NIR spectral ranges. Additionally, a quartz tungsten halogen (QTH) illumination source 140, which is also referred to as a halogen lamp in this disclosure, generates a broad spectrum of light that includes UV, VIS, NIR, VIS-NIR, SWIR, eSWIR, NIR-eSWIR, MIR, and LWIR ranges.

During operation, the VIS and/or NIR light is transmitted via the endoscope 102 to a target 104. Also during operation, the light generated by the halogen lamp illumination source 140 is transmitted via the endoscope 102 to the target 104. After the photons from both illumination sources 100, 140 interact with the target 104, the interacted photons are transmitted through the endoscope 102 along the optical path 101 and into an optic 120. The optic 120 transmits VIS-NIR light, but reflects SWIR light. The VIS-NIR light that is transmitted by the optic 120 travels to a first camera chip 110A, which is a VIS-NIR FPA. Critically, in this embodiment, the VIS-NIR FPA does not have a CF or MCF placed between it and the optic 120, and thus the VIS-NIR light is transmitted to the FPA without such filtering. The optic 120 also reflects SWIR light to a second camera chip 110B, which is a SWIR FPA. Further, this embodiment includes a SWIR CF or MCF 130B placed in the optical path 101 between the SWIR FPA camera chip 110B and the optic 120 to modulate the broadband light source. The configuration illustrated in this embodiment can be beneficial because the illuminations sources can be synced to alternately illuminate the target to prevent interference between the broadband and tunable light source optical paths.

Processes for Target Discrimination

Figure 9:
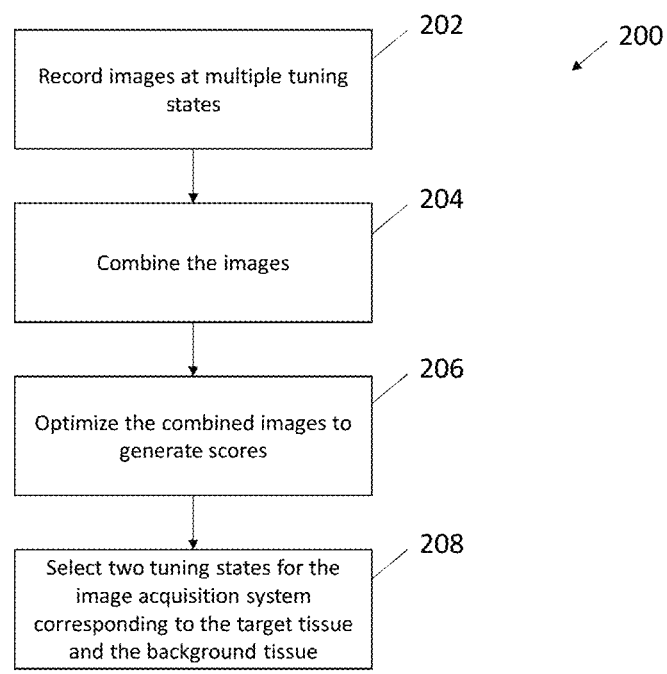
FIG. 9 illustrates a process for selecting tuning states of an image acquisition system for target discrimination.

As noted above, in some embodiments a process can be executed by a computer system to generate a target score image from two or more sample images (i.e., a T1 image and a T2 image), which can fuse the two or more sample images. One example of such a process 200 is illustrated in FIG. 9. The steps executed by the computer system can be embodied as software, hardware, firmware, or combinations thereof. In one embodiment, the steps executed by the computer system can be embodied as instructions stored in a memory of the computer system that, when executed by a processor coupled to the memory, cause the computer system to perform the process 200. In another embodiment, the steps executed by the computer system can be embodied as a field-programmable gate array (FPGA) or an application-specific integrated circuit (ASIC), for example. In various embodiments, the process 200 can be used in connection with any of the embodiments of imaging systems illustrated in FIGS. 1-7, which are described above.

Figure 10A:
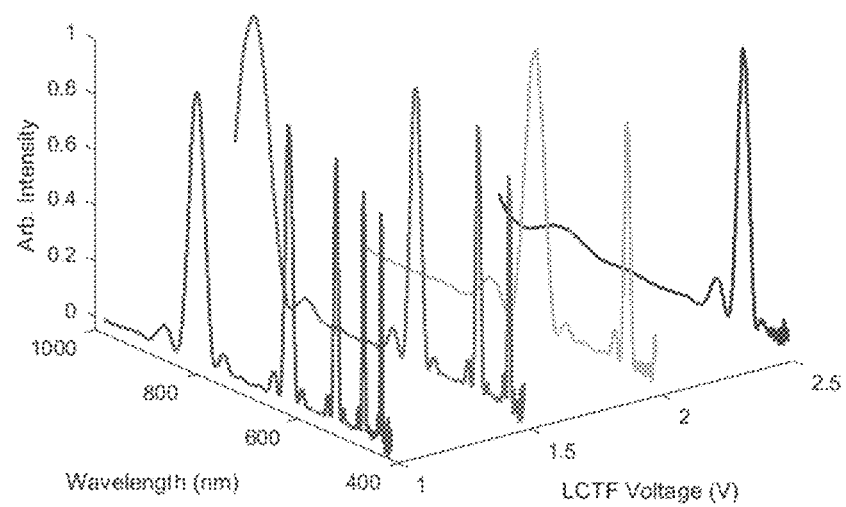
FIG. 10A illustrates a plot demonstrating various tuning states for an LCTF stage.
Figure 10B:
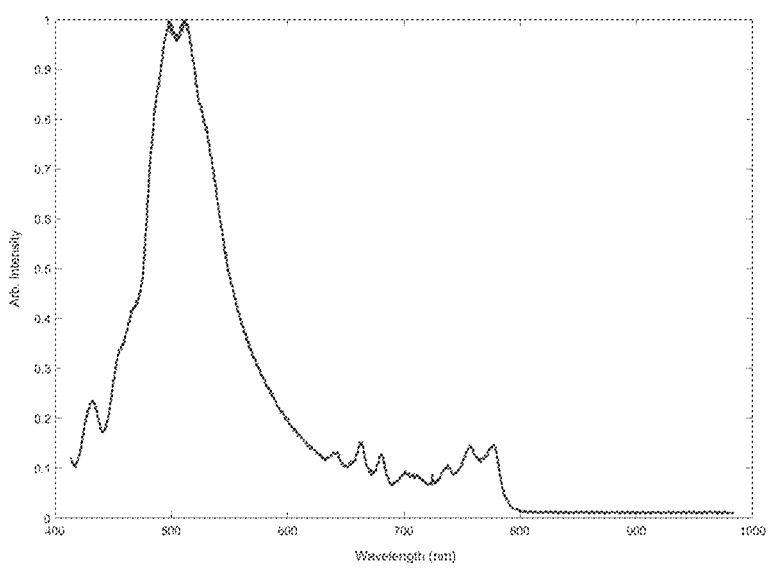
FIG. 10B illustrates a plot demonstrating a tunable LED illumination source output.
Figure 10C:
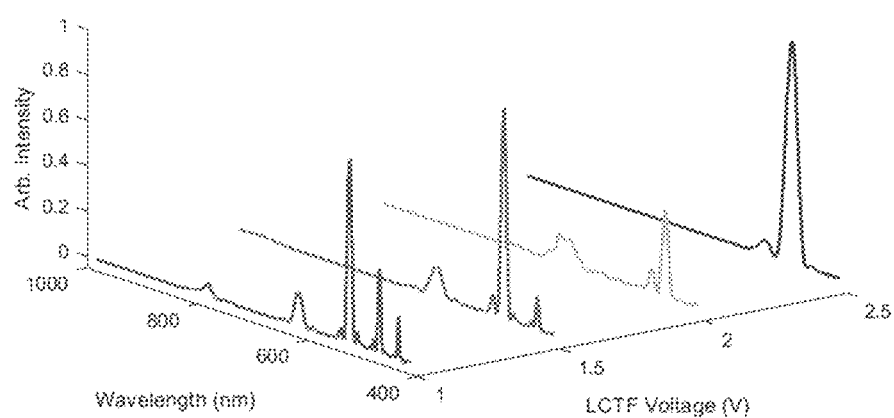
FIG. 10C illustrates a plot demonstrating a combined profile of tunable LED illumination source output and selected LCTF tuning states.
Figure 10D:
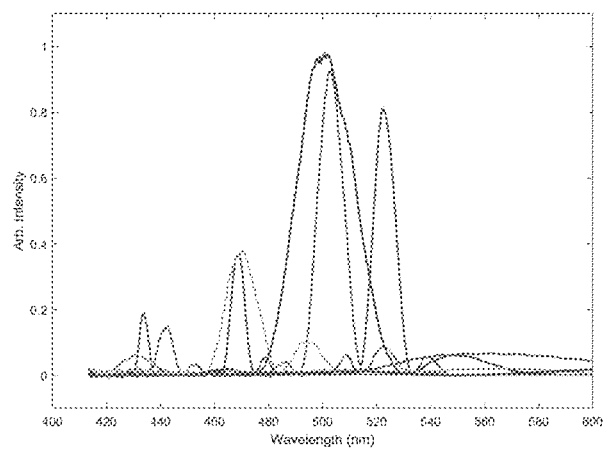
FIG. 10D illustrates an overlapped view of the plot shown in FIG. 10C.

As noted above, the tunable LED illumination source 100; LCTF stage 108, 108A, 108b or CF/MCF 130, 130A, 130B; and the camera chip(s) 110, 110A, 110B can be synched for data (i.e., image) collection. In some embodiments, the tunable LED illumination source 100 can be maintained at a constant output and the LCTF, CF, or MCF stage can be tuned. In other embodiments, the LCTF, CF, or MCF stage can be configured to provide a specific output and the tunable LED illumination source 100 can be tuned. In still other embodiments, both the tunable LED illumination source 100 and the LCTF, CF, or MCF stage can be tuned. The particular manner in which the various components of the image acquisition system are tuned can be referred to as a "tuning state" for the image acquisition system. Accordingly, the computer system can record 202 an image at multiple different tuning states for the image acquisition system. In one embodiment, the computer system can record 202 an image at each different possible tuning state of the image acquisition system. A first image can be referred to as a T1 image, a second image can be referred to as a T2 image, and so on. Further, the computer system can combine 204 the recorded images into a single file. In one embodiment, the recorded images can be combined 204 into hypercubes. Accordingly, the computer system can optimize 206 the hypercubes to generate scores. In one embodiment, the computer system could execute, for example, a particle swarm optimization (PSO) algorithm to optimize the hypercubes. Accordingly, the computer system can select 208 two tuning states for the image acquisition system based on the calculated scores, wherein one of the tuning states is optimized for the background tissue and the other of the tuning states is optimized for the target tissue. To illustrate these concepts, FIG. 10A illustrates a plot of various tuning states for an LCTF stage 108 and FIG. 10B illustrates a plot of the tunable output of an LED illumination source. Notably, the output of the LED illumination source 100 can be held constant for convolution with various LCTF 108 tuning states or different LED outputs and LCTF tuning states can be selected during the image recordation process. The tuning states for an LCTF stage 108 and the output of the LED illumination source 100 can be selected during the optimization process to identify the tuning states of the image acquisition system that correspond to the target tissue and the background tissue. Further, FIGS. 10C and 10D illustrate plots for various tuning states of the image acquisition system (i.e., various combinations of tuning states of the LCTF stage 108 and LED output). Each of the tuning states can define different spectral profiles for the image acquisition system. Accordingly, the different spectral profiles can correspond to different target and background tissues and, thus, can be used to visualize a variety of different anatomical structures, as desired by the user. Note that although the plots described above were discussed in terms of the image acquisition system having an LCTF stage 108, it should be recognized that this was simply for illustrative purposes and the image acquisition can be in the form of a variety of different embodiments having different configurations and components, as discussed above. In sum, the process 200 can be used to define different tuning states for the image acquisition system for discrimination of a target tissue from background tissue.

Figure 11:
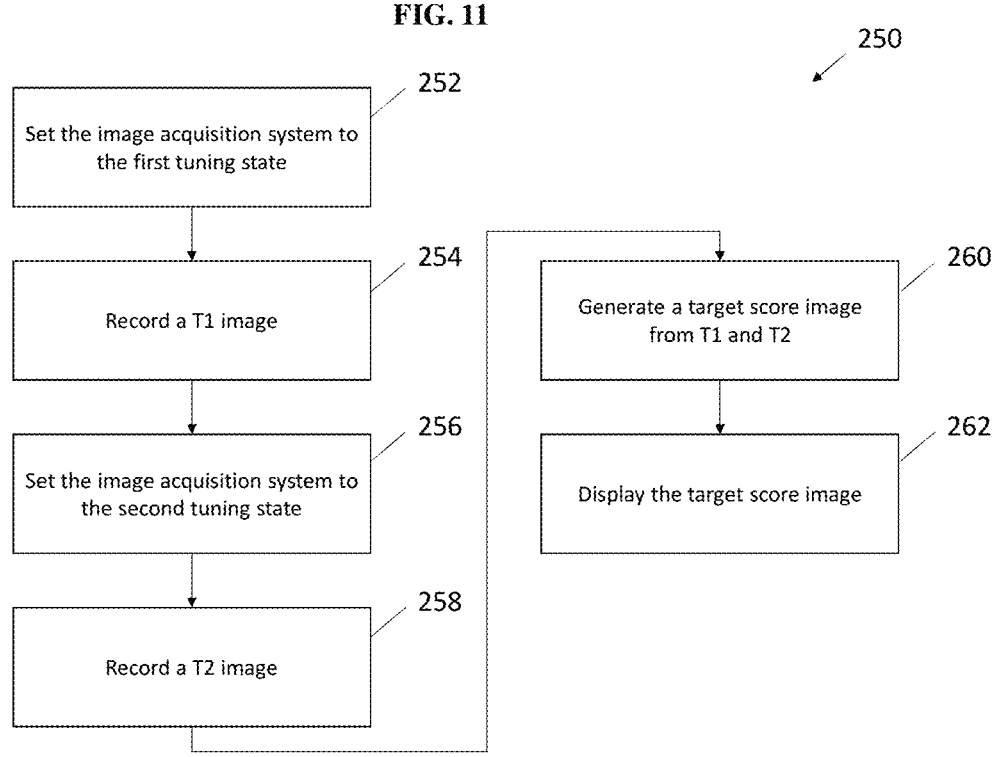
FIG. 11 illustrates a process executed by an image acquisition system for target discrimination.

Referring now to FIG. 11, there is shown a process 250 for the various embodiments of the image acquisition systems that can be executed once the tuning states have been selected for the target and background tissues. In execution, the image acquisition system can iteratively transition between the two selected tuning states, record both images sequentially, complete its analysis, and display a score image generated from the images. In particular, the image acquisition can set 252 to a first tuning state, record 254 a first image (T1), set 256 to a second tuning state, record 258 a second image (T2), generate 260 a target score image from the images, and display 262 the target score image. In some embodiments, the process 250 can be executed in real-time. The systems and processes described herein are beneficial because they are specifically adapted for generating score images with contrast that highlights the target tissue from background tissues in real-time.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. An apparatus comprising:
   an illumination source that is configured to emit light, the light comprising at least one of ultraviolet (UV), visible (VIS), near infrared (NIR), visible-near infrared (VIS-NIR), shortwave infrared (SWIR), extended shortwave infrared (eSWIR), near infrared-extended shortwave infrared (NIR-eSWIR), mid-wave infrared (MIR), or long-wave infrared (LWIR) light;
   an optical filter;
   at least one camera chip; and
   an optical path configured to direct the light emitted by the first illumination source at a biological sample and direct the light reflected from the biological sample to the at least one camera chip;
   wherein the illumination source and the optical filter are transitionable between a first tuning state corresponding to a target tissue of the biological sample and a second tuning state corresponding to a background tissue of the biological sample;
   wherein the at least one camera chip is configured to:
      record a first image when the illumination source and the optical filter are in the first tuning state,
      record a second image when the illumination source and the optical filter are in the second tuning state, and
      generate a score image corresponding to the target tissue based on the first image and the second image.

2. The apparatus of claim 1, wherein the illumination source comprises at least one of a light emitting diode (LED), supercontinuum laser, organic light emitting diode (OLED), electroluminescent device, fluorescent light, gas discharge lamp, metal halide lamp, xenon arc lamp, and induction lamp.

3. The apparatus of claim 1, wherein the illumination source comprises a first illumination source, the apparatus further comprising a second illumination source that emits at least one of UV, VIS, NIR, VIS-NIR, SWIR, eSWIR, NIR-eSWIR MIR, or LWIR light.

4. The apparatus of claim 1, wherein the optical filter is selected from the group consisting of a liquid crystal filter, a liquid crystal on silicon (LCoS) that can be controlled to alter the luminous flux in near real time or in real time, and a rotating filter wheel, a MCF, and a CF.

5. The apparatus of claim 1, wherein the at least one camera chip comprises a first camera chip and a second camera chip.

6. The apparatus of claim 5, further comprising an optic coupled to the optical path, the optic configured to direct a first portion of the light emitted by the first illumination source at the first camera chip for generating the first image from the first portion of the light and direct a second portion of the light emitted by the first illumination source at the second camera chip for generating the second image from the second portion of the light.

7. The apparatus of claim 1, wherein the at least one camera chip comprises a focal plane array sensitive to at least one of UV, VIS, NIR, VIS-NIR, SWIR, eSWIR, NIR-eSWIR MIR, or LWIR light.

8. A method of analyzing a biological sample, the method comprising:
   emitting light from an illumination source that is configured to emit at least one of ultraviolet (UV), visible (VIS), near infrared (NIR), visible-near infrared (VIS-NIR), shortwave infrared (SWIR), extended shortwave infrared (eSWIR), near infrared-extended shortwave infrared (NIR-eSWIR), mid-wave infrared (MIR), or long-wave infrared (LWIR) light;
   transmitting the light via an optical path through an optical filter;
   wherein the illumination source and the optical filter are transitionable between a first tuning state corresponding to a target tissue of the biological sample and a second tuning state corresponding to a background tissue of the biological sample;
   collecting the light on at least one camera chip;
   recording a first image when the illumination source and the optical filter are in the first tuning state;
   recording a second image when the illumination source and the optical filter are in the second tuning state; and
   generating a score image corresponding to the target tissue based on the first image and the second image.

9. The method of claim 8, wherein the illumination source comprises at least one of a light emitting diode (LED), supercontinuum laser, organic light emitting diode (OLED), electroluminescent device, fluorescent light, gas discharge lamp, metal halide lamp, xenon arc lamp, and induction lamp.

10. The method of claim 8, wherein the illumination source comprises at least one of a light emitting diode (LED), supercontinuum laser, and organic light emitting diode (OLED).

11. The method of claim 8, wherein the illumination source comprises a first illumination source, the apparatus further comprising a second illumination source that emits at least one of UV, VIS, NIR, VIS-NIR, SWIR, eSWIR, NIR-eSWIR MIR, or LWIR light.

12. The method of claim 8, wherein the optical filter is selected from the group consisting of a liquid crystal filter, a liquid crystal on silicon (LCoS) that can be controlled to alter the luminous flux in near real time or in real time, a rotating filter wheel, a MCF, and a CF.

13. The method of claim 8, wherein the at least one camera chip comprises a first camera chip and a second camera chip.

14. The method of claim 13, wherein collecting the light on at least one camera chip comprises:
  directing, via an optic coupled to the optical path, a first portion of the light emitted by the illumination source at the first camera chip for generating the first image from the first portion of the light; and
  directing, via the optic, a second portion of the light emitted by the illumination source at the second camera chip for generating the second image from the second portion of the light.

15. The method of claim 8, wherein the at least one camera chip comprises a focal plane array sensitive to at least one of UV, VIS, NIR, VIS-NIR, SWIR, eSWIR, NIR-eSWIR MIR, or LWIR light.

\* \* \* \* \*